United States Patent [19]

Chasar

[11] Patent Number: 4,522,735
[45] Date of Patent: Jun. 11, 1985

[54] POLYPHOSPHORAMIDITE OLIGOMERS AND STABILIZER COMPOSITIONS THEREOF

[75] Inventor: Dwight W. Chasar, Northfield, Ohio

[73] Assignee: The B. F. Goodrich Company, Akron, Ohio

[21] Appl. No.: 505,516

[22] Filed: Jun. 17, 1983

[51] Int. Cl.$^3$ .................. C07D 203/06; C07D 205/04; C07D 211/06; C07D 265/30

[52] U.S. Cl. .................. 252/49.9; 44/57; 44/63; 44/72; 44/76; 44/78; 106/243; 106/263; 106/270; 106/285; 252/400 A; 252/401; 252/402; 252/403; 260/239 A; 260/239 B; 260/926; 426/541; 544/157; 544/337; 546/21; 548/412; 564/12; 524/83; 524/86; 524/96; 524/97; 524/98; 524/99; 524/100; 524/101; 524/102; 524/104

[58] Field of Search .................. 252/400, 49.9, 401, 252/402, 403; 260/239 A, 239 B, 926; 544/57, 157, 337; 546/21; 548/412; 564/12; 524/83, 86, 96, 97, 98, 99, 100, 101, 102, 104, 105, 115, 121; 426/241; 106/243, 263, 270, 285; 44/57, 63, 72, 76, 78

[56] References Cited

U.S. PATENT DOCUMENTS

| | | | |
|---|---|---|---|
| 3,354,240 | 11/1967 | Pochowicz | 252/400 |
| 3,531,483 | 9/1970 | Gilles | 544/221 |
| 4,436,811 | 3/1984 | Fryberg et al. | 430/564 |

FOREIGN PATENT DOCUMENTS

| | | | |
|---|---|---|---|
| 0042359 | 12/1981 | European Pat. Off. | 544/57 |
| 0070254 | 1/1983 | European Pat. Off. | 544/57 |

*Primary Examiner*—Henry R. Jiles
*Assistant Examiner*—J. G. Mullins
*Attorney, Agent, or Firm*—J. Hughes Powell, Jr.; Alan A. Csontos

[57] ABSTRACT

Amines are reacted with phosphorous trichloride to form N-dichlorophosphinoamines that are then reacted with a bisphenol in about equimolar amounts to provide polyphosphoramidite oligomers. The polyphosphoramidite oligomers are effective as stabilizers for polymers such as polyolefins, and form even more efficient stabilizer combinations with hydroxyphenylalkyleneyl isocyanurates.

18 Claims, No Drawings

POLYPHOSPHORAMIDITE OLIGOMERS AND STABILIZER COMPOSITIONS THEREOF

BACKGROUND OF THE INVENTION

A variety of organic phosphite compounds have been prepared and proposed for use as stabilizers, particularly to protect polymers from the degradative effects of heat and oxygen. Some of these materials have been used with varying degrees of success, and some of them have found use in combination with hydroxyphenylalkyleneyl isocyanurates to enhance the activity of the isocyanurates. Improved, less expensive, phosporous containing compounds that are useful as polymer stabilizers, and particularly those which form useful combinations with the hydroxyphenylalkyleneyl isocyanurates are desired, along with increased resistance to hydrolysis in polymer applications.

SUMMARY OF THE INVENTION

Polyphosphoramidite oligomers are readily and economically prepared by reacting N-dichlorophosphinoamines with bisphenols. The polyphosphoramidite oligomers are effective stabilizers to protect polymers, including polyolefins, from the degradative effects of heat and oxygen. These polyphosphoramidite oligomers also form useful stabilizer compositions with hydroxyphenylalkyleneyl isocyanurates.

DETAILED DESCRIPTION

The polyphosphoramidite oligomers may be represented by the formula

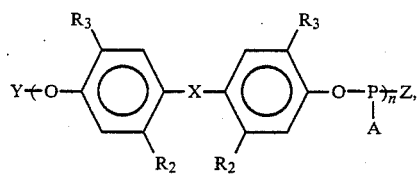

wherein: A is a nitrogen radical

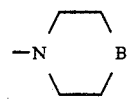 (1)

wherein $R_1$ is an alkyl radical containing 1 to 4 carbon atoms,

 (2)

wherein a is 3 to 6, or

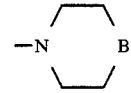 (3)

where B is —O—, —S—, or —NR; $R_2$ and $R_3$ are hydrogen, primary, secondary or tertiary alkyl radicals containing 1 to 4 carbon atoms; and perferably $R_3$ is an alkyl radical, more preferably t-butyl; X is $>CH_2$, $>CHCH_3$, $>CHCH_2CH_3$, $>CHCH_2CH_2$—$CH_3$, $>C(CH_3)_2$, —O—, —S—, $>SO$, or $>SO_2$; Y is H or

wherein Q is Cl or OH; Z is Cl, OH, or

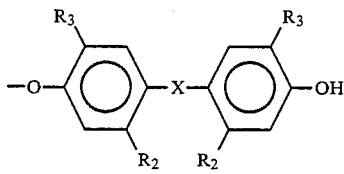

wherein $R_2$, $R_3$ and X have the meanings given above; and n is 2 to 10.

More preferably, in (1) $R_1$ contains 4 carbon atoms; in (2) a is 4 to 5; in (3) B is —O—; $R^3$ is t-butyl; X is $>CHCH_2CH_3$, $>C(CH_3)_2$ or $>CHCH_2CH_2CH_3$; in Y Q is OH; Z is OH or

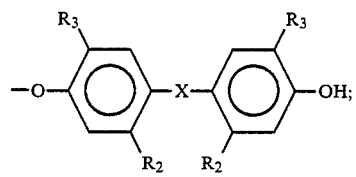

and n is 2 to 5.

The oligomeric phosphoramidites are prepared by the reaction of N-dichlorophosphinoamines with bisphenols in the presence of an alkyl amine.

The N-dichlorophospinoamines have the formula A-P-CL$_2$ wherein A is

wherein $R_1$ is an alkyl radical containing 1 to 4 carbon atoms,

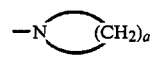

wherein a is 3 to 6 or

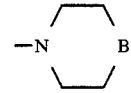

wherein B is —O—, —S—, or $NR_1$.

Representative N-dichlorophospinoamines are N-dichlorophospino-dimethylamine, N-dichlorophospinodiethylamine, N-dichlorophospino-dipropylamine, N-dichlorophospino-diisopropylamine, N-dichlorophospino-di-n-butylamine, N-dichlorophospino-di-isobutylamine, N-dichlorophospino-di-isobutylamine, N-dichlorophospinoazetidine, N-dichlorophospinopyrrolidine, N-dichlorophospino-piperidine, N-dichlorophospino-morpholine, N-dichlorophospino-thiomorpholine, and the like.

The bisphenols have the formula

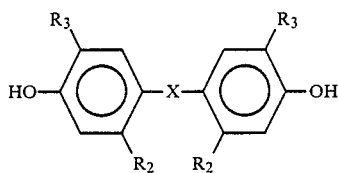

wherein $R_2$ and $R_3$ are hydrogen, a primary, secondary or tertiary alkyl radical containing 1 to 4 carbon atoms and X is $>CH_2$, $>CHCH_3$, $>CHCH_2CH_3$, $>CHCH_2CH_2CH_3$, $>C(CH_3)_2$, $-O-$, $-S-$, $>SO$, or $>SO_2$.

Typical bisphenols include 4,4'-methylidene bis(2-t-butylphenol), 4,4'-ethylidene bis(2-t-butylphenol), 4,4'-propylidene bis(2-t-butylphenol), 4,4'-isopropylidene bis(2-t-butylphenol), 4,4'-n-butylidene bis(2-t-butylphenol), 4,4'-oxy bis(2-ti-butylphenol), 4,4'-thio bis(2-t-butylphenol), 4,4'-sulfinyl bis(2-t-butylphenol), 4,4'-sulfonyl bis(2-t-butylphenol), 4,4'-methylidene bis(2-t-butyl-5-methylphenol), 4,4'-ethylidene bis(2-t-butyl-5-methylphenol), 4,4'-propylidene bis(2-t-butyl-5-methylphenol), 4,4'-isopropylidene bis(2-t-butyl-5-methylphenol), 4,4'-n-butylidene bis(2-t-butyl-5-methylphenol), 4,4'-oxy bis(2-t-butyl-5-methylphenol), 4,4'-thio bis(2-t-butyl-5-methylphenol), 4,4'-sulfinyl bis(2-t-butyl-5-methylphenol), 4,4'-sulfonyl bis(2-t-butyl-5-methylphenol), 4,4'-methylidene bis(2-t-butyl-5-t-butylphenol), 4,4'-ethylidene bis(2-t-butyl-5-t-butylphenol), 4,4'-propylidene bis(2-t-butyl-5-t-butylphenol), 4,4'-isopropylidene bis(2-t-butyl-5-t-butylphenol), 4,4'-n-butylidene bis(2-t-butyl-5-butylphenol), 4,4'-oxy bis(2-t-butyl-5-t-butylphenol), 4,4'-thio bis(2-t-butyl-5-t-butylphenol), 4,4'-sulfinyl bis(2-t-butyl-5-t-butylphenol), 4,4'-sulfonyl bis(2-t-butyl-5-t-butylphenol), 4,4'-methylidene bis(2-t-butyl-5-isopropylphenol), 4,4'-ethylidene bis(2-t-butyl-5-isopropylphenol), 4,4'-propylidene bis(2-t-butyl-5-isopropylphenol), 4,4'-isopropylidene bis(2-t-butyl-5-isopropylphenol), 4,4'-n-butylidene bis(2-t-butyl-5-isopropylphenol), 4,4'-oxy bis(2-t-butyl-5-isopropylphenol), 4,4'-thio bis(2-t-butyl-5-isopropylphenol), 4,4'-sulfinyl bis(2-t-butyl-5-isopropylphenol), 4,4'-sulfonyl bis(2-t-butyl-5-isopropylphenol), and the like.

Representative polyphosphoramidite oligomers are poly{[N,N-pentamethylene][4,4'-butylidene bis(2-t-butyl-5-methylphenyl)]phosphoramidite}, poly{[N,N-pentamethylene][4,4'isopropylidene bis(2-t-butylphenyl)]phosphoramidite}, poly{[N,N-oxydiethylene][4,4'-isopropylidene bis(2-t-butylphenyl)]phosphoramidite}, poly{[N,N-oxydiethylene][4,4'-butylidene bis(2-t-butyl-5-methylphenyl)]phosphoramidite}, poly{[N,N-oxydiethylene][4,4'-thio bis(2-t-butyl-5-methylphenyl)]phosphoramidite}, poly{[N,N-di-n-butyl][4,4'-butylidene bis(2-t-butyl-5-methylphenyl)]phosphoramidite}, poly{[N,N-di-n-butyl][4,4'-thio bis(2-t-butyl-5-methylphenyl)]phosphoramidite}, poly{[N,N-di-isopropyl][4,4'-butylidene bis(2-t-butyl-5-methylphenyl)]phosphoramidite}, poly{[N,N-di-isopropyl][4,4'-thio bis(2-t-butyl-5-methylphenyl]phosphoramidite}, poly{[N,N-di-isopropyl][4,4'-isopropylidene bis(2-t-butylphenyl)]phosphoramidite}, poly{[N,N-di-n-propyl][4,4'-butylidene bis(2-t-butyl-5-methylphenyl)]phosphoramidite}, poly{[N,N-di-n-propyl][4,4'-thiobis(2-t-butyl-5-methylphenyl)]phosphoramidite}.

The hydroxyphenylalkyleneyl isocyanurate compounds used in combination with the polyphosphoramidites of this invention have the formula

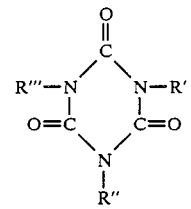

wherein R' is a hydroxyphenylalkyleneyl radical of the formula

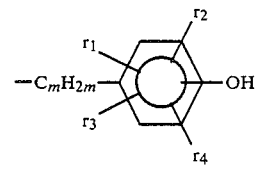

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R''' are hydrogen, an alkyl radical containing 1 to 18 carbon atoms, or are the same as R'. A more preferred compound is when R" and R''' are equal to R', i.e., all the R groups are hydroxyphenylalkyleneyl radicals, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m is 1.

Even more preferred are the symmetrical tris(3,5-di-tert-alkyl-4-hydroxybenzyl)isocyanurates of the formula

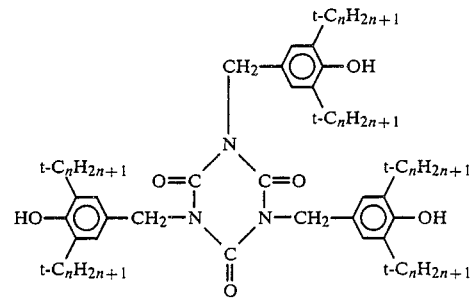

wherein n is 4 to 8.

Examples of the 4-hydroxybenzyl isocyanurate compounds are: tris(3-t-butyl-4-hydroxybenzyl)isocyanurate, tris(3-cetyl-4-hydroxybenzyl)isocyanurate, tris(3,5-dimethyl-4-hydroxybenzyl)isocyanurate, tris(3-methyl-5-isopropyl-4-hydroxybenzyl)isocyanurate, tris(3,5-di-t-butyl-4-hydroxybenzyl)isocyanurate, tris(3-t-butyl-5-t-amyl-4-hydroxybenzyl)isocyanurae, tris[3,5-di(1-methyl-1-ethylpropyl)-4-hydroxybenzyl]isocyanurate, tris[3,5-di-(1,1,2,2-tetramethylpropyl)-4-hydroxybenzyl]isocyanurate, bis(3,5-dimethyl-4-hydroxybenzyl)isocyanurate, (3-methyl-4-hydroxybenzyl)isocyanurate, (3-t-butyl-4-hydroxybenzyl)isocyanurate and the like. Reference is made to U.S. Pat. No. 3,531,483 which discloses isocyanurate compounds encompassed by this invention. This disclosure of this patent is incorporated herein by reference.

The amount of polyphosphoramidite oligomer used may vary from about 0.01 to 10 weight parts per 100 weight parts of material to be stabilized. More usually about 0.1 to 5.0 parts are used for mixtures with the hydroxyphenylalkyleneyl isocyanurate. The hydroxyphenylalkyleneyl isocyanurate compound is used at a level from about 0.01 part to about 1 to 5 parts by weight, and more preferably at from about 0.05 part to about 3 parts by weight per 100 parts by weight of the organic material. The polyphosphoramidite oligomer compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.05 to 5 parts by weight per 100 parts by weight of organic material. The hydroxyphenylalkyleneyl isocyanurate can be used in from about 10:1 to 1:10 weight ratio of isocyanurate compound to the polyphosphoramidite oligomer compound. Excellent results are obtained at about a 3:1 to 1:3 weight ratio. A 1:1 weight ratio of the compounds provides effective stabilization of organic materials.

In the following examples, the oligomeric phosphoramidites were prepared by dissolving one-half to preferably one equivalent of the N-dichlorophosphinoamine and about one equivalent of bisphenol in triethylamine and refluxing the mixture for 10 to 20 hours. The reaction mixture was cooled, filtered, and the filtrate evaporated to dryness. The resulting glassy product was converted to a powder by washing it with methanol and drying. The expected structures were confirmed by infrared spectroscopy and the molecular weights by field desorption mass spectrometry and vapor phase osmometry.

EXAMPLE I

Poly{[N,N-pentamethylene][4,4'-isopropylidene bis(2-t-butylphenyl) ]phosphoramidite}

2.73 grams (0.015 mol) of N-dichlorophosphinopiperidine and 5 grams (0.015 mol) of 4,4'-isopropylidene-bis(2-t-butylphenol) were dissolved in 50 ml of triethylamine and the mixture refluxed for 20 hours. The dried glass was washed with methanol to provide 4.5 grams of a white powder having a melting point of 104°–155° C. The number average ($\overline{M}n$) molecular weight was 1154.

EXAMPLE II

Poly{[N,N-pentamethylene][4,4'-butylidene bis(2-t-butyl-5-methylphenyl)]phosphoramidite}

4.87 grams (0.026 mol) of N-dichlorophosphinopiperidine and 10 grams (0.026 mol) of 4,4'-butylidene bis(2-t-butyl-5-merthylphenol) were added to 50 ml of triethylamine and refluxed for 20 hours. The dried white powder product had a melting point of 128°–162° C. The ($\overline{M}n$) molecular weight was 1744.

EXAMPLE III

N,N-pentamethylene bis{2-t-butyl-4-[2-methyl-2-(3-t-butyl-4-hydroxyphenyl)ethyl]}phosphoramidite 1.38 grams (0.007 mol) of N-dichlorophosphino piperidine and 5.0 grams (0.015 mol) of 4,4'-isopropylidene bis(2-t-butylphenol) were added to 50 ml of triethylamine and the mixture was refluxed for 20 hours. The reaction mixture was filtered and the filtrate evaporated to dryness. The dry product was washed with methanol and dried. 4.3 grams of N,N-pentamethylene bis{2-t-butyl-4-[2-methyl-2-(3-t-butyl-4-hydroxyphenyl)ethyl]} phosphoramidite was obtained. This material was an off-white color. The molecular weight (FD/MS) was 793.

Test samples of the polyphosphoramidite oligomer in polypropylene were prepared by mixing the stabilizer compounds with polypropylene in a Brabender Plasticorder fitted with a Cam-Head (mixing chamber). The polypropylene is first masticated for 1½ minuutes at 190° C. Then the stabilizer is added, followed by 3 minutes additional mixing. The mass is removed and pressed into 20 mil thick sheets. From these sheets are cut 1"×1" plaques for oven aging. Type C (3"33⅛") tensil bars are cut for UV stability tests.

Thermal/oxidative stability (oven aging) testing consisted of aging the samples in triplicate in an air-circulating oven at 125° C. The time to catastrophic crumbling (failure) of the plaque was measured and reported as days to failure.

Each sample contained 0.1 weight part of stabilizer per 100 weight parts of polypropylene. The following results were obtained:

Poly{[N,N-pentamethylene][4,4'-isopropylidene bis(2-t-butylphenyl)]phosphoramidite}: 26⅓ days.

Poly{[N,N-pentamethylene]4,4'-butylidene bis(2-t-butyl-5-methylphenyl)]phosphoramidite}: 14⅔ days.

N,N-pentamethylene bis{2-t-butyl-4-[2-methyl-2-(3-t-butyl-4-hydroxyphenyl)ethyl]}phosphoramidite: 12⅓ days.

To demonstrate the unexpected synergistic enhancement of antioxidant activity when the polyphosphoramidite oligomers of this invention are combined with a hydroxyphenylalkyleneyl isocyanurate, test samples of polypropylene with 0.05 weight part each of tris(3,5-di-t-butyl-4-hydroxybenzyl)isocyanurate and the polyphosphoramidites listed below were prepared and tested in the air oven until failure. The results obtained were as follows:

Poly{[N,N-pentamethylene][4,4'-isopropylidene bis(2-t-butylphenyl)]phosphoramidite}: 39⅓ days.

Poly{[N,N-pentamethylene][4,4'-butylidene bis(2-t-butyl-5-methylphenyl)]phosphoramidite}: 45 days.

N,N-pentamethylene bis{2-t-butyl-4-[2-methyl-2-(3-t-butyl-4-hydroxyphenyl)ethyl]}phosphoramidite: 26⅓ days.

Following the procedure of these Examples, a series of polyphosphoramidite oligomers were prepared. About 0.014 mol of each reactant was used, dissolved in 50 ml of triethylamine.

N-dichlorophosphinodibutylamine was reacted with:

(1) 4,4'-butylene bis(2-t-butyl-5-methylphenol) to yield 3.6 grams of poly{[N,N-di-n-butyl][4,4'-butylidene bis(2-t-butyl-5-methylphenyl)]phosphoramidite}, an off-white powder, melting point 97°–122° C. $\overline{M}n$ is 1775.

(2) 4,4'-thio bis(2-t-butyl-5-methylphenol) to yield 6.4 grams of poly{[N,N-di-n-butyl][4,4'-thiobis(2-t-butyl-5-methylphenyl)]phosphoramidite}, an off-white powder, melting point 112°–125° C.

N-dichlorophospino-diisopropylamine was reacted with (3) 4,4'-butylidene bis(2-t-butyl-5-methylphenol) to yield 0.2 grams of poly{[N,N-di-isopropyl][4,4'-butylidene bis(2-t-butyl-5-methylphenyl)]phosphoramidite}, an off-white powder, melting point 132°–167° C.

(4) 4,4'-thiobis(2-t-butyl-5-methylphenol) to yield 5.0 grams of poly{[N,N-di-isopropyl][4,4'-thiobis(2-t-butyl-5-methylphenyl)]phosphoramidite}, an off-white powder, melting point 148°–167° C.

(5) 4,4'-isopropylidene-bis(-2-t-butylphenol) to yield 4.0 grams of poly{[N,N-di-isopropyl][4,4'-isopropylidene bis(2-t-butylphenyl)]phosphoramidite}, an off-white powder, melting point 111°–126° C.

N-dichlorophosphino-di-n-propylamine was reacted with (6) 4,4'-butylidene bis(2-t-butyl-5-methylphenol) to yield poly{[N,N-di-n-propyl][4,4'-butylidene bis(2-butyl-5-methylphenyl)]phosphoramidite}, a tan powder, melting point 113°–126° C.

(7) 4,4'-thiobis(2-t-butyl-5-methylphenol) to yield 5.6 grams of poly{[N,N-di-n-propyl][4,4'-thiobis(2-t-butyl-5-methylphenyl)]phosphoramidite}, an off-white powder, melting point 125°–133° C.

N-dichlorophosphinomorpholine was reacted with:

(8) 4,4'-isopropylidene-bis(2-t-butylphenol) to yield 6 grams of poly{[N,N-oxydiethylene][4,4'-isopropylidene bis(2-t-butylphenyl)]phosphoramidite}, a white powder, melting point 138°–160° C., $\overline{M}n$ is 1895.

(9) 4,4'-butylidene bis(2-t-butyl-5-methylphenol) to yield 0.68 grams of poly{[N,N-oxydiethylene][4,4'-butylidene bis(2-t-butyl-5-methylphenyl)]phosphoramnidite}, a white powder, melting point 144°–240° C.

And

(10) 4,4'-thiobis(2-t-butyl-5-methylphenol) to yield poly{[N,N-oxydiethylene][4,4'-thiobis(2-t-butyl-5-methylphenyl)]phosphoramidite}, a tan powder, melting point 162°–175° C., $\overline{M}n$ is 2387.

The combination of isocyanurate compound and the polyphosphoramidite oligomers provide exceptional heat stability to polyolefin polymers. The combination is especially useful for the statilization of α-monoolefin homopolymers and copolymers, wherein the α-monoolefin contains 2 to about 8 carbon atoms. High and low-density polyethylene, isotactic and atactic polypropylene, poly-isobutylene, and poly(4-methyl-1-pentene) have excellent resistance to heat and oxygen when stabilized with the combinations of the present invention. Ethylene-propylene copolymers and ethylene-propylene terpolymers, generally containing less than about 10 percent by weight of one or more monomers containing multiple unsaturation provided, for example, by 1,4-hexadiene, dimethyl-1, 4,9-decatriene, dicyclopentadiene, vinyl norborene, ethylidene norbornene, and the like, also provide excellent ageing properties using the composition of this invention.

Other organic materials which can be stabilized in accordance with the present invention include both natural and synthetic polymers. For example, the stabilizers are useful for the sttabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as poly(vinyl chloride), poly(vinylidene chloride), copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates, and the like; epihalohydrin polymers; polyether- or polyol-derived polyurethanes; acetal homopolymers and copolymers; polycarbonates; polyesters such as those derived from maleic, fumaric, itaconic, or terephthalic anhydrides; for example, polyethylene terephthalate; polyamides such as those derived from the reaction of hexamethylenediamine with adipic or sebacic acid; epoxy resins such as those obtained from the condensation of epichlorophydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline and the like.

The compounds are readily incorporated into materials to be patented by dissolving or dispersing them with the materials, in liquids, dispersions, solutions, and solid forms. If the material is a solid, especially a polymeric solid such as rubber or a plastic, the compounds can be admixed using mixers such as Banburys, extruders, two-roll mills, and the like, following conventional techniques. One way to disperse the compounds in plastic materials is to dissolve or suspend the compounds in a solvent or diluent, mix the mixture with a plastic in powder or solution form, and then evaporate the solvent.

Compositions containing the novel compounds and combination of compounds can also contaiñ other known compounding ingredients such as fillers like carbon black, silica, metal carbonates, talc, and the like; pigments and colorants; curative ingredients like sulfur and peroxides, and vulcanization accelerators; fungicides; processing aids, reinforcing agents and standard ingredients known to the art. Other ingredients known in the art as ultra violet light, thermal and/or oxidative stabilizers can also be used in the stabilized compositions.

I claim:
1. Polyphosphoramidite oligomers having the formula

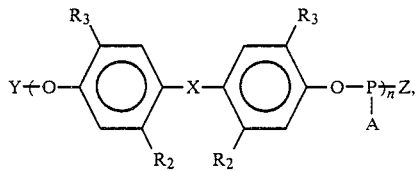

wherein: A is

 (1)

wherein $R_1$ is an alkyl radical containing 1 to 4 carbon atoms,

wherein a is 3 to 6, or

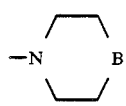

wherein B is —O—; $R_2$ and $R_3$ are hydrogen, primary, secondary or tertiary alkyl radicals containing 1 to 4 carbon atoms; X is $>CH_2$, $>CHCH_3$, $>CHCH_2CH_3$, $>CHCH_2CH_2CH_3$, $>C(CH_3)_2$,; Y is H or

wherein Q is Cl or OH; Z is Cl, OH, or

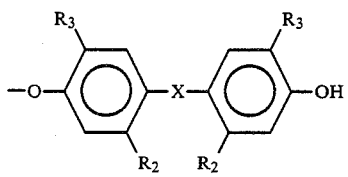

wherein $R_2$, $R_3$ and X have the meanings given above; and n is 2 to 10.

2. Polyphosphoramidite oligomers of claim 1 wherein in (1) $R_1$ contains 4 carbon atoms; in (2) a is 4 to 5; in (3) B is —O—; $R_3$ is t-butyl; X is $>CHCH_2CH_3$, $>C(CH_3)_2$, $>CHCH_2CH_2CH_3$; in Y Q is OH; Z is OH or

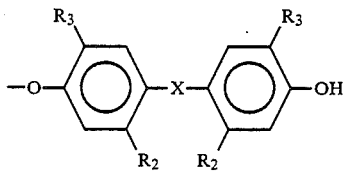

and n is 2 to 5.

3. Polyphosphoramidite oligomers of claim 2 selected from the group consisting of poly{[N,N-pentamethylene][4,4'-isopropylidene bis(2-t-butyphenyl)]phosphoramidite}, poly{[N,N-pentamethylene][4,4'-butylidene bis(2-t-butyl-5-methylphenyl)]phosphoramidite}, poly{[N,N-di-n-butyl][4,4'-butylidene bis(2-t-butyl-5-methylphenyl)]phosphoramidite}, poly{[N,N-di-n-butyl][4,4'-thiobis(2-t-butyl-5-methylphenyl)]phosphoramidite}, poly{[N,N-di-isopropyl][4,4'-butylidene bis(2-t-butyl-5-methylphenyl)]phosphoramidite}, poly{[N,N-di-isopropyl][4,4'-isopropylidene bis(2-t-butylphenyl)]phosphoramidite}, poly{[N,N-di-n-propyl][4,4'-butylidene bis(2-t-butyl-5-methylphenyl)]phosphoramidite}, poly{[N,N-di-n-propyl][4,4'-thiobis(2-t-butyl-5-methylphenyl)]phosphoramidite}, poly{[N,N-oxydiethylene][4,4'-isopropylidene bis(2-t-butylphenyl)]phosphoramidite}, poly{[N,N-oxydiethylene][4,4'-butylidene bis(2-t-butyl-5-methylphenyl)]phosphoramidite}, and poly{[N,N-oxydiethylene][4,4'-thio bis(2-t-butyl-5-methylphenyl)]phosphoramidite} poly{[N,N-di-isopropyl][4,4'-thiobis(2-t-butyl-5-methylphenyl)]phosphoramidite}.

4. A composition comprising natural and synthetic polymer, petroleum, animal and vegetable oil, fat and wax organic materials subject to thermal and oxidative degradation and stabilizing amounts of polyphosphoramidite oligomers having the formula

wherein: A is

wherein $R_1$ is an alkyl radical containing 1 to 4 carbon atoms;

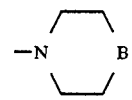

wherein a is 3 to 6, or

wherein B is —O—; $R_2$ and $R_3$ are hydrogen, primary, secondary or tertiary alkyl radicals containing 1 to 4 carbon atoms; X is $>CH_2$, $>CHCH_3$, $>CHCH_2CH_3$, $>CHCH_2CH_2CH_3$, $>C(CH_3)_2$; Y is H or $$Q-P- \atop A$$

wherein Q is Cl or OH; Z is Cl, OH or

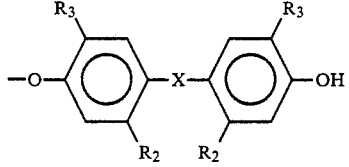

wherein $R_2$, $R_3$ and X have the meanings given above; and n is 2 to 10.

5. A composition of claim 4 wherein said organic material is selected from the group consisting of α-monoolefin homopolymers and copolymers, wherein the α-monoolefin contains 2 to about 8 carbon atoms, high and low-density polyethylene, isotactic and atactic polypropylene, poly-isobutylene, poly(4-methyl-1-pentene), ethylene-propylene copolymers, ethylene-propylene terpolymers containing less than 10 percent by weight of one or more monomers containing multiple unsaturation, 1,4-hexadiene, dimethyl-1,4,9-decatriene, dicylcopentadiene, vinyl norborene and ethylidene norborene; natural rubber; halogenated rubber; conjugated diene polymers, polybutadiene, copolymers of butadiene with styrene, acrlonitrile, acrylic acid, alkyl acrylates or methacrylates, methyl vinyl ketone and vinyl pyridine; polyisoprene; polychloroprene, poly(vinyl chloride); poly(vinylidene chloride); copolymers of vinyl chloride with vinylidene chloride; polyvinyl acetate; copolymers of vinyl halide with butadiene, styrene, vinyl esters, α,β-unsaturated ketones and aldehydes; homopolymers and copolymers of acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates; epihalohydrin polymers; polyether- and polyol-derived polyurethanes; acetal homopolymers and copolymers; polycarbonates; polyesters derived from maleic, fumaric, itaconic or terephthalate; polyamides derived from the reaction of hexamethylenediamine with adipic or sebacic acid; epoxy resin, condensations of epichlorohydrin with bisphenols; and ring opened olefin polymers; waxes; synthetic and petroleum derived lubricating oils and greases; animal oils; fat tallow, lard, cod-liver oil, sperm oil; vegetable oils, castor, linseed, peanut, palm, and cotton seed; fuel oil; diesel oil and gasoline; and in (1) $R_1$ contains 4 carbon atoms; in (2) a is 4 to 5; in (3) B is —O—; $R_3$ is t-butyl; X is >CHCH$_2$CH$_3$, >C(CH$_3$)$_2$, >CHCH$_2$CH$_2$CH$_3$; in Y Q is OH; Z is OH or

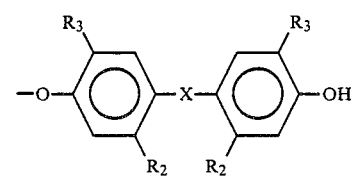

and n is 2 to 5.

6. A composition of claim 5 wherein said polymer is a polyolefin and said polyphosphoramidite oligomers are selected from the group consisting of poly{[N,N-pentamethylene][4,4'-isopropylidene bis(2-t-butylphenyl)]phosphoramidite}, poly{[N,N-pentamethylene][4,4'-butylidene bis(2-t-butyl-5-methylphenyl)]phosphoramidite}, poly{[N,N-di-n-butyl][4,4'-butylidene bis(2-t-butyl-5-methylphenyl)]phosphoramidite}, poly{[N,N-di-n-butyl][4,4'-thiobis(2-t-butyl-5-methylphenyl)]phosphoramidite}, poly{[N,N-di-isopropyl][4,4'-butylidene bis(2-t-butyl-5-methylphenyl)]phosphoramidite}, poly{[N,N-di-isopropylidene bis(2-t-butylphenyl)]phosphoramidite}, poly{[N,N-di-n-propyl][4,4'-butylidene bis(2-t-butyl-5-methylphenyl)]phosphoramidite}, poly{[N,N-di-n-propyl][4,4'-thiobis(2-t-butyl-5-methylphenyl)]phosphoramidite}, poly{[N,N-oxydiethylene][4,4'-isopropylidene bis(2-t-butylphenyl)]phosphoramidite}, poly{[N,N-oxydiethylene][4,4'-butylidene bis(2-t-butyl-5-methylphenyl)]phosphoramidite}, and poly{[N,N-oxydiethylene][4,4'-thio bis(2-t-butyl-5-methylphenyl)]phosphoramidite} poly{[N,N-di-isopropyl][4,4'-thiobis(2-t-butyl-5-methylphenyl)]phosphoramidite}.

7. A stabilizer composition comprising (1) polyphosphoramidite oligomers having the formula

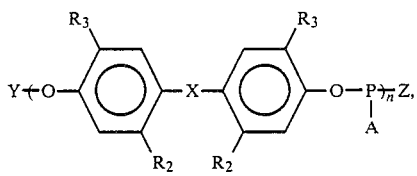

wherein: A is

 (1)

wherein $R_1$ is an alkyl radical containing 1 to 4 carbon atoms,

 (2)

wherein a is 3 to 6, or

 (3)

wherein B is —O—; $R_2$ and $R_3$ are hydrogen, primary, secondary or tertiary alkyl radicals containing 1 to 4 carbon atoms; X is >CH$_2$, >CHCH$_3$, >CHCH$_2$CH$_3$, >CHCH$_2$CH$_2$CH$_3$, >C(CH$_3$)$_2$,; Y is H or

wherein Q is Cl or OH; Z is Cl, OH, or

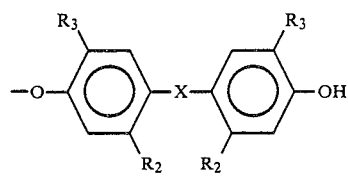

wherein $R_2$ and $R_3$ and X have the meanings given above; and n is 2 to 10; and (2) hydroxyphenylalkyleneyl isocyanurates of the formula

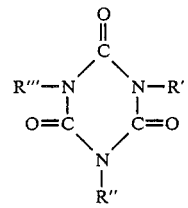

wherein R' is a hydroxyphenylalkyleneyl radical of the formula

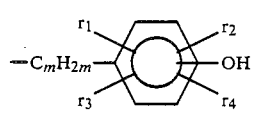

wherein m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R″ and R‴ are hydrogen, an alkyl radical containing 1 to 18 carbon atoms, or are the same as R′.

8. A stabilizer composition of claim 7 wherein in (1) $R_1$ contains 4 carbon atoms; in (2) a is 4 to 5; in (3) B is —O—; $R_3$ is t-butyl; X is >CHCH$_2$CH$_3$, >C(CH$_3$)$_2$, >CHCH$_2$CH$_2$CH$_3$; in Y Q is OH; Z is OH or

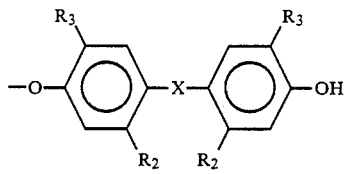

and n is 2 to 5; and in (2) R″ and R‴ are equal to R′, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m is 1.

9. A stabilizer composition of claim 8 wherein (1) is selected from the group consisting of poly{[N,N-pentamethylene][4,4′-isopropylidene bis(2-t-butylphenyl)]phosphoramidite}, poly{[N,N-pentamethylene][4,4′-butylidene bis(2-t-butyl-5-methylphenyl)]phosphoramidite}, poly{[N,N-di-n-butyl][4,4′-butylidene bis(2-t-butyl-5-methylphenyl)]phosphoramidite}, poly{[N,N-di-n-butyl][4,4′-thiobis(2-t-butyl-5-methylphenyl)]phosphoramidite}, poly{[N,N-di-isopropyl][4,4′-butylidene bis(2-t-butyl-5-methylphenyl)]phosphoramidite}, poly{[N,N-di-isopropyl][4,4′-isopropylidene bis(2-t-butylphenyl)]phosphoramidite}, poly {[N,N-di-n-propyl][4,4′-butylidene bis(2-t-butyl-5-methylphenyl)]phosphoramidite}, poly{[N,N-di-n-propyl][4,4′-thiobis(2-t-butyl-5-methylphenyl)]phosphoramidite}, poly{[N,N-oxydiethylene][4,4′-isopropylidene bis(2-t-butylphenyl)]phosphoramidite}, poly{[N,N-oxydiethylene][4,4′-butylidene bis(2-t-butyl-5-methylphenyl)]phosphoramidite}, and poly{[N,N-oxydiethylene][4,4′-thio bis(2-t-butyl-5-methylphenyl)]phosphoramidite} poly{[N,N-di-isopropyl][4,4′-thiosbis(2-t-butyl-5-methylphenyl)]phosphoramidite}; and (2) has the formula

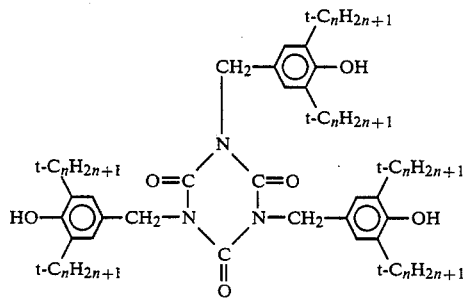

wherein n is 4 to 8.

10. A stabilizer composition of claim 9 wherein (2) is 1,3,5-tris(3,5-di-t-butyl-4-hydroxybenzyl)isocyanurate.

11. A composition of claim 11 wherein in (1) $R_1$ contains 4 carbon atoms; in (2) a is 4 to 5; in (3) B is —O—; $R_3$ is t-butyl; X is >CHCH$_2$CH$_3$, >C(CH$_3$)$_2$, >CHCH$_2$CH$_2$CH$_3$; in Y Q is OH; Z is OH or

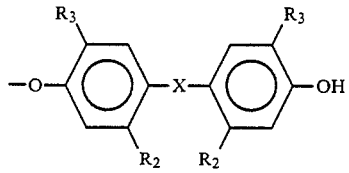

and n is 2 to 5; and in (2) R″ and R‴ are equal to R′, i.e., all the R groups are hydroxyphenylalkyleneyl radicals, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m is 1.

12. A composition of claim 11 wherein (1) is selected from the group consisting of poly{[N,N-pentamethylene][4,4′-isopropylidene bis(2-t-butylphenyl)]phosphoramidite}, poly{[N,N-pentamethylene][4,4′-butylidene bis(2-t-butyl-5-methylphenyl)]phosphoramidite}, poly{[N,N-di-n-butyl][4,4′-butylidene bis(2-t-butyl-5-methylphenyl)]phosphoramidite}, poly{[N,N-di-n-butyl][4,4′-thiobis(2-t-butyl-5-methylphenyl)]phosphoramidite}, poly{[N,N-di-isopropyl][4,4′-butylidene bis(2-t-butyl-5-methylphenyl)phosphoramidite}, poly{[N,N-di-isopropyl][4,4′-isopropylidene bis(2-t-butylphenyl)]phosphoramidite}, poly{[N,N-di-n-propyl][4,4′-butylidene bis(2-t-butyl-5-methylphenyl)]phosphoramidite}, poly{[N,N-di-n-propyl][4,4′-thiobis(2-t-butyl-5-methylphenyl)]phosphoramidite}, poly{[N,N-oxydiethylene][4,4′-isopropylidene bis(2-t-butylphenyl)]phosphoramidite}, poly{[N,N-oxydiethylene][4,4′-butylidene bis(2-t-butyl-5-methylphenyl)]phosphoramidite}, and poly{[N,N-oxydiethylene][4,4′-thiobis(2-t-butyl-5-methylphenyl)]phosphoramidite} poly{[N,N-di-isopropyl][4,4′-thiobis(2-t-butyl-5-methylphenyl)]phosphoramidite}; and (2) has the formula

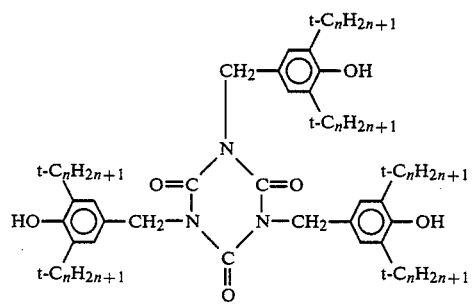

wherein n is 4 to 8.

13. A composition of claim 12 wherein (2) is 1,3,5-tris(3,5-di-t-butyl-4-hydroxybenzyl)isocyanurate.

14. A composition comprising natural and synthetic polymer, petroleum, animal and vegetable oil, fat and wax organic materials subject to thermal and oxidative degradation and stabilizing amounts of polyphosphoramidite oligomers having the formula

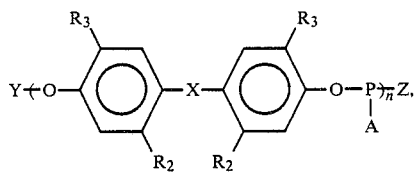

wherein: A is

wherein $R_1$ is an alkyl radical containing 1 to 4 carbon atoms;

wherein a is 3 to 6, or

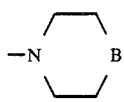

wherein B is —O—; $R_2$ and $R_3$ are hydrogen, primary, secondary or tertiary alkyl radicals containing 1 to 4 carbon atoms; X is >CH$_2$, >CHCH$_3$, >CHCH$_2$CH$_3$, >CHCH$_2$CH$_2$CH$_3$, >C(CH$_3$)$_2$; Y is H or

wherein Q is Cl or OH; Z is Cl, OH or

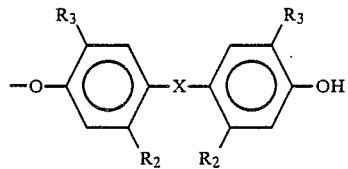

wherein $R_2$, $R_3$ and X have the meanings given above; and n is 2 to 10; and (2) hydroxyphenylalkyleneyl isocyanurates having the formula

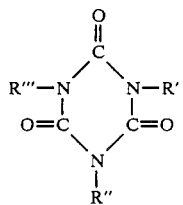

wherein R' is a hydroxyphenylalkyleneyl radical of the formula

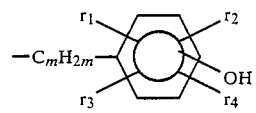

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R″ and R‴ are hydrogen, an alkyl radical containing 1 to 18 carbon atoms, or are the same as R′.

15. A composition of claim 14 wherein said organic material is selected from the group consisting of α-monoolefin homopolymers and copolymers, wherein the α-monoolefin contains 2 to about 8 carbon atoms, high and low-density polyethylene, isotactic and atactic polypropylene, poly-isobutylene, poly(4-methyl-1-pentene), ethylene-propylene copolymers, ethylene-propylene terpolymers containing less than 10 percent by weight of one or more monomers containing multiple unsaturation, 1,4-hexadiene, dimethyl-1,4,9-decatriene, dicylcopentadiene, vinyl norborene and ethylidene norborene; natural rubber; halogenated rubber; conjugated diene polymers, polybutadiene, copolymers of butadiene with styrene, acrylonitrile, acrylic acid, alkyl acrylates or methacrylates, methyl vinyl ketone and vinyl pyridine; polyisoprene; polychloroprene, poly(vinyl chloride); poly(vinylidene chloride); copolymers of vinyl chloride with vinylidene chloride; polyvinyl acetate; copolymers of vinyl halide with butadiene, styrene, vinyl esters, α,β-unsaturated ketones and aldehydes; homopolymers and copolymers of acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates; epihalohydrin polymers; polyether- and polyol-derived polyurethanes; acetal homopolymers and copolymers; polycarbonates; polyesters derived from maleic, fumaric, itaconic or terephthalate; polyamides derived from the reaction of hexamethylenediamine with adipic or sebacic acid; epoxy resin, condensations of epichlorohydrin with bisphenols; and ring opened olefin polymers; waxes; synthetic and petroleum derived lubricating oils and greases; animal oils; fat, tallow, lard, cod-liver oil, sperm oil; vegetable oils, castor, linseed, peanut, palm, and cotton seed; fuel oil; diesel oil and gasoline, and in (1) $R_1$ contains 4 carbon atoms; in (2) a is 4 to 5; in (3) B is —O—; $R_3$ is t-butyl; X is >CHCH$_2$CH$_3$, >C(CH$_3$)$_2$, >CHCH$_2$CH$_2$CH$_3$; in Y Q is OH; Z is OH or

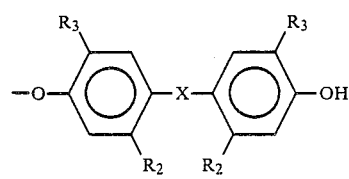

and n is 2 to 5.

16. A composition of claim 11 wherein said organic material is a polyolefin.

17. A composition of claim 12 wherein said organic material is a polyolefin.

18. A composition of claim 13 wherein said organic material is a polyolefin.

* * * * *

UNITED STATES PATENT AND TRADEMARK OFFICE
CERTIFICATE OF CORRECTION

PATENT NO. : 4,522,735
DATED : June 11, 1985
INVENTOR(S) : DWIGHT W. CHASAR

It is certified that error appears in the above-identified patent and that said Letters Patent are hereby corrected as shown below:

In Claim 1, column 8, line 52, "Polyphosphcramidite oligomers" should read -- A polyphosphoramidite oligomer--

Claim 1, column 9, line 15 " $>CHCH_2CH_2CH_3$, $>C(CH_3)_2$, Y is H or" should read -- $>CHCH_2CH_2CH_3$, $>C(CH_3)_2$, or S; Y is H or--

Claim 2, column 9, line 33 "Polyphosphoramidite oligomers" should read --A polyphosphoramidite oligomer--

Claim 3, column 9, line 48 "Polyphosphoramidite oligomers" should read --A polyphosphoramidite oligomer--

Claim 4, column 10, line 3 "A composition comprising natural and synthetic" should read --A composition comprising a member selected from the group consisting of natural and synthetic--

Claim 4, column 10, line 37 " $>CHCH_2CH_2CH_3$, $>C(CH_3)_2$; Y is H or" should read -- $>CHCH_2CH_2CH_3$, $>C(CH_3)_2$ or S; Y is H or--

Claim 6, column 11, lines 42, 43 "a polyolefin and said polyphosphoramidite oligomers are selected from" should read --a polyolefin and said a polyphosphoramidite oligomer is selected from--

Claim 7, column 11, line 66 "polyphosphoramidite oligomers" should read --a polyphosphoramidite oligomer--

UNITED STATES PATENT AND TRADEMARK OFFICE
CERTIFICATE OF CORRECTION

PATENT NO. : 4,522,735
DATED : June 11, 1985
INVENTOR(S) : DWIGHT W. CHASAR

It is certified that error appears in the above-identified patent and that said Letters Patent are hereby corrected as shown below:

Column 12, line 31, ">CHCH$_2$CH$_2$CH$_3$, >C(CH$_3$)$_2$; Y is H or" should read -- >CHCH$_2$CH$_2$CH$_3$, >C(CH$_3$)$_2$; or S, Y is H or --.

Claim 14, column 14, line 63 "a composition comprising natural and synthetic" should read --a composition comprising a member selected from the group consisting of natural and synthetic--

Claim 14, column 15, line 34 ">CHCH$_2$CH$_3$, >C(CH$_3$)$_2$; Y is H or" should read -->CHCH$_2$CH$_2$CH$_3$, >C(CH$_3$)$_2$; or S, Y is H or--

Signed and Sealed this

Fifth Day of August 1986

[SEAL]

Attest:

DONALD J. QUIGG

Attesting Officer

Commissioner of Patents and Trademarks